United States Patent
Diamond (12)

(10) Patent No.: US 6,544,521 B2
(45) Date of Patent: Apr. 8, 2003

(54) IMMUNOREACTIVE PEPTIDE CTL EPITOPES OF HUMAN CYTOMEGALOVIRUS PP150

(75) Inventor: Don J. Diamond, Glendora, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/983,019

(22) Filed: Oct. 22, 2001

(65) Prior Publication Data

US 2002/0146820 A1 Oct. 10, 2002

Related U.S. Application Data

(60) Provisional application No. 60/241,944, filed on Oct. 20, 2000.

(51) Int. Cl.⁷ .................. A61K 38/08; A61K 39/245; A61K 35/12; C12N 15/86; C12Q 1/70

(52) U.S. Cl. ................. 424/186.1; 424/230.1; 424/93.7; 530/327; 514/15; 435/5; 435/235.1; 435/320.1

(58) Field of Search .................... 424/186.1, 230.1, 424/199.1, 93.1, 93.21, 93.7, 93.71; 435/235.1, 320.1, 5; 514/15; 530/327

(56) References Cited

U.S. PATENT DOCUMENTS

| | | |
|---|---|---|
| 5,075,213 A | 12/1991 | Pande et al. |
| 5,405,940 A | 4/1995 | Boon et al. |
| 5,470,730 A | 11/1995 | Greenberg et al. |
| 5,635,363 A | 6/1997 | Altman et al. |

FOREIGN PATENT DOCUMENTS

| | | |
|---|---|---|
| EP | 0 252 531 A1 | 1/1988 |
| WO | WO 9205794 | 4/1992 |
| WO | WO 94/00150 | 1/1994 |
| WO | WO 9606929 | 3/1996 |
| WO | WO 97/40165 | 10/1997 |
| WO | WO 98/02746 A1 | 1/1998 |
| WO | WO 98/26074 | 6/1998 |
| WO | WO 99/19349 | 4/1999 |
| WO | WO 00/75180 | 6/2000 |

OTHER PUBLICATIONS

Novak et al. Journal of General Virology 72:1409–1413, 1991.*

Moldoveanu et al., "CpG DNA, a Novel Immune Enhancer for Systemic and Mucosal Immunization with Influenza Virus," *Vaccine*, 16:11/12:1216–1224, 1998.

Pande et al., "Human Cytomegalovirus Strain Towne pp65 Gene: Nucleotide Sequence and Expression in *Escherichia Coli*," *Virology*, 182:220–228, 1991.

Alexander et al., "Development of High Potency Universal DR–Restricted Helpter Epitopes by Modification of High Affinity DR–Blocking Peptides," Immunity 1:751–761, Dec. 1994.

Allen et al., "Induction of AIDS Virus–Specific CTL Activity in Fresh, Unstimulated Peripheral Blood Lymphocytes from Rhesus Macques Vaccinated with a DNA Prime/Modified Vaccinia Virus Ankara Boost Regimen," The J. of Immunology 164:4968–4978, 2000.

Altman et al., "NIAID Tetramer Core Facility," Research at the VRC, http://www.emory.edu/WHSC/YERKES/VRC/tetramer.html, Oct. 16, 2001, pp. 1–2.

Bertoletti et al., "Definition of a Minimal Optimal Cytotoxic T–Cell Epitope within the Hepatitis B Virus Nucleocapside Protein", Journal of Virology 67(4):2376–2380 (1993).

Borysiewicz et al., "Human Cytomegalovirus–Specific Cytotoxic T Lymphocytes: Requirements for in vitro Generation and Specificity", Eur. J. Immunol. 13:804–809 (1983).

Borysiewicz et al., "Relative Frequency of Stage–Specific CTL Recognizing the 72–kD Immediate Early Protein and Glycoprotein B Expressed by Recombinant Vaccinia Viruses", J. Exp. Med. 168:919–931 (1988).

Clark et al., "Isolation and Partial Chemical Characterization of a 64,000–Dalton Glycoprotein of Human Cytomegalovirus", Journal of Virology, Notes 49(1):279–282 (1984).

D'Amaro et al., "A Computer Program for Predicting Possible Cytotoxic T Lymphocyte Epitopes Based on HLA Class I Peptide–Binding Motifs", Human Immunology 43:13–18 (1995).

Deres et al., "In vivo priming of virus–specific cytotoxic T lymphocytes with synthetic lipopeptide vaccine," Nature 342:561–564 (1989).

Drijfhout et al., "Detailed Motifs for Peptide Binding to HLA–A*0201 Derived from Large Random Sets of Peptides Using a Cellular Binding Assay", Human Immunology 43:1–12 (1995).

Forman et al., "A 64,000 Dalton Matrix Protein of Human Cytomegalovirus Induces In Vitro Immune Responses Similar to Those of Whole Viral Antigen", The Journal of Immunology, 134(5):3391–3395 (1985).

Gilbert et al., "Selective Interference with Class I Major Histocompatibility Complex Presentation of the Major Immediate–Early Protein Following Infection with Human Cytomegalovirus", Journal of Virology 67(6):3461–3469 (1993).

Gonczol E. et al., "Preclinical evaluation of an ALVAC (canarypox)–human cytomegalovirus glycoprotein B vaccine candidate," Vaccine 13(12):1080–1085 (1995).

(List continued on next page.)

Primary Examiner—Mary E. Mosher
(74) Attorney, Agent, or Firm—Rothwell, Figg, Ernst & Manbeck

(57) ABSTRACT

The invention provides peptides which are immunogenic epitopes recognized by CD8+ class I MHC restricted cytotoxic T-lymphocytes of patients harboring latent cytomegalovirus (HCMV) infection. The peptides are capable of activating CTL in the absence of active viral replication, and thus are useful for eliciting a cellular immune response against HCMV by normal and immunodeficient subjects. Vaccines against HCMV, with and without adjuvants, and immunological and diagnostic reagents are disclosed.

16 Claims, No Drawings

OTHER PUBLICATIONS

Goodrich et al., "Ganciclovir Prophylaxis To Prevent Cytomegalovirus Disease after Allogeneic Marrow Transplant", Annals of Internal Medicine 118:173–178 (1993).

Goodrich et al., "Early Treatment with Ganciclovir to Prevent Cytomegalovirus Disease After AllogenicBone Marrow Transplantation", The New England Journal of Medicine 325(23):1601–1607 (1991).

Gyulai et al., "Cytotoxic T Lymphocyte (CTL) Responses to Human Cytomegalovirus pp65, IE1–Exon4,gB, pp150 and pp28 in Healthy Individuals: Reevaluation of Prevalence of IE1–Specific CTLs," The J. of Infectious Diseases 181:1537–1546, 2000.

Ishioka et al., "Utilization of MHC Class I Transgenic Mice for Development of Minigene DNA Vaccines Encoding Multiple HLA–Restricted CTL Epitopes," The J. of Immunology 162:3915–3925, 1999.

Kast et al., "Human Leukocyte Antigen–A2.1 Restricted Candidate Cytotoxic T Lymphocyte Epitopes of Human Papillomavirus Type 16 E6 and E7 Proteins Identified by Using the Processing–Defective Human Cell Line T2", Journal of Immunotherapy 14:115–120 (1993).

Kern et al., "Target Structures of the CD8$^+$–T Cell Response to Human Cytomegalovirus: the 72–Kilodalton Major Immediate–Early Protein Revisited," J. of Virology 73(10):8179–8184, Oct. 1999.

Lacey et al., "Cytotoxic Function of CMV–pp65–Specific CD8$^+$ T–lymphocytes Correlates with Frequencies Measured by HLA Tetramers in Recipients of Stem cell Transplants,—Tetramer Analysis of HSCT Recipients," study supported by grants from Research Supplement for Under–Represented Minorities, Comprehensive Cancer Center and the General Clinical Research Center, pp 1–26 and 12 Figures, 2001.

La Rosa et al., "Enhanced immune activity of cytotoxic T–lymphocyte epitope analogs derived from positional scanning synthetic combinatorial libraries," Blood 97(6):1776–1786, Mar. 15, 2001.

Li et al., "Recovery of HLA–Restricted Cytomegalovirus (CMV)–Specific T–Cell Responses After Allogeneic Bone Marrow Transplant: Correlation with CMV Diseas and Effect of Ganciclovir Proophylaxis", Blood 83(7):1971–1979 (1994).

Lubaki et al., "A Novel Method for Detection and ex Vivo Expansion of HIV Type 1–Specific Cytolytic T Lymphocytes", Aids Research and Human Retroviruses 10(11):1427–1431, 1994.

McLaughlin–Taylor et al., "Identification of the Major Late Human Cytomegalovirus Matrix Protein pp65 as a Target Antigen for CD8+ Virus–Specific Cytotoxic T Lymphocytes", Journal of Medical Virology 43:103–110 (1994).

Miller et al., "Design of Retrovirus Vectors for Transfer and Expression of the Human β–Globin Gene", Journal of Virology 62(11):4337–4345 (1988).

Missale et al., "HLA–A31 and HLA–Aw68–Restricted Cytotoxic T Cell Responses to a Single Hepatitis B Virus Nucleocapsid Epitope During Acute Viral Hepatitis", J. Exp. Med. 177:751–762 (1993).

Moss, "Vaccinia Virus Vectors", Construction of Recombinant Viruses, Chapter 15, pp. 345–362.

Oseroff et al., "Pools of lipidated HTL–CTL constructs prime for multiple HBV and HCV CTL epitope responses," Vaccine 16(8):823–833, 1998.

Pande et al., "Direct DNA Immunization of Mice with Plasmid DNA Encoding the Tegument Protein pp65 (ppUL83) of Human Cytomegalovirus Induces High Levels of Circulating Antibody to the Encoded Protein", Scand J Infect Dis Suppl 99, (Sweden) 1995 p 117–120.

Pande et al., "Structural Analysis of a 64–kDa Major Structural Protein of Human Cytomegalovirus (Towne): Identification of a Phosphorylation Site and Comparison to pp65 of HCMV (AD169)", Virology 178:6–14 (1990).

Parker, K. et al., "Scheme for Ranking Potential HLA–A2 Binding Peptides Based on Independent Binding of Individual Peptide Side–Chains," Journal of Immunology 152:163–175 (1994).

Quinnan et al., "HLA–Restricted T–Lymphocyte and Non–T–Lymphocyte Cytotoxic Responses Correlate with Recovery from Cytomegalovirus Infection in Bone–Marrow–Transplant Recipients", The New England Journal of Medicine, Cytomegalovirus Infection 307(1):7–13 (1982).

Ralston et al., "Characterization of Hepatitis C Virus Envelope Glycoprotein Complexes Expressed by Recombinant Vaccinia Viruses", Journal of Virology 67(11):6753–6761 (1993).

Rasmussen, "Immune Response to Human Cytomegalovirus Infection", Current Topics in Microbiology and Immunology 154:222–254 (1990).

Retiére et al., "Generation of Cytomegalovirus–Specific Human T–Lymphocyte Clones by Using Autologous B–Lymphoblastoid Cells with Stable Expression of pp65 or IE1 Proteins: a Tool to Study the Fine Specificity of the Antiviral Response," J. Of Virology 74(9):3948–3952, May 2000.

Reusser et al., "Cytotoxic T–Lymphocyte Response to Cytomegalovirus After Human Allogeneic Bone Marrow Transplantation: Pattern of Recovery and Correlation With Cytomegalovirus Infection and Disease", Blood 78(5):1373–1380(1991).

Riddell et al., "Therapeutic Reconstitution of Human Viral Immunity by Adoptive Transfer of Cytotoxic T Lymphocyte Clones", CurrentTopics in Microbiology and Immunology 189:9–34 (1994).

Riddell et al., "Restoration of Viral Immunodeficient Humans by the Adoptive Transfer of T Cell Clones", Science 257:238–241 (1992).

Speir et al., "Potential Role of Human Cytomegalovirus and p53 Interaction in Coronary Restenosis", Science 265:391–394 (1994).

Tobery et al., "Cutting Edge: Induction of Enhanced CTL–Dependent Protective Immunity In Vivo by N–End Rule Targeting of a Model Tumor Antigen," The J. of Immunology 162:639–642, 1999.

Townsend et al., "Recognition of Influenza Virus Proteins by Cytotoxic T Lymphocytes", Phil. Trans. R. Soc. Lond. B 323:527–533 (1989).

Tsung et al., "Gene Expression and Cytopathic Effect of Vaccinia Virus Inactivated by Psoralen and Long–Wave UV Light," J. of Virology 70(1):165–171, Jan. 1996.

Tsunoda T. et al., "Seriologically identically HLA B35 alleles which do not cross–present minimal cytotoxic epitopes to CD8+CTL," J. Cell. Biochem. vol. Suppl. 0(19A):298, Abstr. No. J2–218 (1995).

Valmori et al., "Induction of Potent Antiturmor CTL Responses by Recombinant Vaccinia Encoding a Melan–A Peptide Analogue," The J. of Immunology 164:1125–1131, 2000.

Vierboom et al., "Peptide Vaccination with an Anchor–Replaced CTL Epitope Protects Against Human Papillomavirus Type 16–Induced Tumors Expressing the Wild–Type Epitope," J. of Immunotherapy 21(6):399–408, 1998.

Vitiello et al., "Development of a Lipopeptide–based Therapeutic Vaccine to Treat Chronic HBV Infection", J. Clin. Invest. 95:341–349 (1995).

Walter et al., "Reconstitution of Cellular Immunity Against Cytomegalovirus in Recipients of Allogeneic Bone Marrow by Transfer of T–Cell Clones from the Donor", The New England Journal of Medicine 333(16):1038–1044 (1995).

Wills, M.R. et al., "The human CTL response to Cytomegalovirus is dominated by structural protein," J. Virology 70:(11):7569–7578 (1996).

Winston et al., "Ganciclovir Prophylaxis of Cytomegalovirus Infection and Disease in Allogeneic Bone Marrow Transplant Recipients", Annals of Internal Medicine 118:179–184 (1993).

Wu et al., "Deoxyribonucleic Acid Vaccines Encoding Antigens With Rapid Proteasome–Dependent Degradation Are Highly Efficient Inducers of Cytolytic T Lymphocytes," The J. of Immunnology 159:6037–6043, 1997.

Yee et al., "Isolation of High Avidity Melanoma–Reactive CTL from Heterogeneous Populations Using peptide–MHC Tetramers," The J. of Immunology 162:2227–2234, 1999.

Zaia et al., "Status of Cytomegalovirus Prevention and Treatment in 2000," American Society of Hematology, pp. 339–355.

Zhou et al., "Association Between Prior Cytomegalovirus Infection and the Risk of Restenosis After Coronary Atherctomy", The New England Journal of Medicine 335(9):624–630 (1996).

Longmate, Jeffrey, et al., "Population Coverage by HLA Class–I Restricted Cytotoxic T–Lymphocyte Epitopes," Immunogenetics 52: 165–173, 2001.

* cited by examiner

IMMUNOREACTIVE PEPTIDE CTL EPITOPES OF HUMAN CYTOMEGALOVIRUS PP150

This application claims priority from prior copending provisional application Serial No. 60/241,944, filed Oct. 20, 2000.

STATEMENT REGARDING FEDERALLY SPONSORED RESEARCH

This invention was made with government support in the form of grant nos. CA30206, CA77544 and CA33572 from the United States Department of Health and Human Services, National Cancer Institute. The government may have certain rights in the invention.

BACKGROUND OF THE INVENTION

1. Technical Field

This invention relates to human cytomegalovirus (HCMV), and in particular to peptide fragments from a protein that produces T-cell epitopes of HCMV in human beings. The peptide fragment epitopes are capable of directing human cytotoxic T lymphocytes (CTL) to recognize and lyse human cells infected with HCMV.

2. Description of the Background Art

The HCMV genome is relatively large (about 235,000 base pairs) and can encode more than two hundred proteins. HCMV comprises a nuclear complex of double-stranded DNA surrounded by capsid proteins having structural or enzymatic functions, and an external glycopeptide- and glycolipid-containing membrane envelope.

HCMV infection is relatively common and is usually self-limiting in the healthy, immunocompetent child or adult (L. Rasmussen, *Curr. Top. Microbiol. Immunol.* 154:221–254 (1990)). However, the virus can cause severe disease in the fetus or infant. For example, HCMV is a common cause of congenital mental retardation in children who acquire the infection in utero from mothers carrying an active infection. Other newborn infants can carry cytomegalovirus for some time before they show symptoms of the disease. Approximately 10% of all newborn infants carry HCMV.

Patients with an active HCMV infection often suffer impairment of at least some of their vital organs, including salivary glands, brain, kidney, liver and lungs. Furthermore, HCMV is associated with a wide spectrum of classical syndromes including mononucleosis and interstitial pneumonia. HCMV also has an oncogenic potential and a possible association with certain types of malignancies, including Kaposi's sarcoma.

Persistent and apparently asymptomatic HCMV infection in an otherwise healthy adult also may pose health risks in certain individuals. For example, individuals who have undergone coronary angioplasty sometimes subsequently develop restenosis as a result of arterial remodeling. In one study, about one third of such patients with restenosis had detectable HCMV DNA in their arterial lesions (E. Speir et al., *Science* 265:391–394 (1994)), whereas in another study al., HCMV seropositive patients were five times more likely to develop restenosis than their seronegative counterparts (Y. F. Zhou et al., *New England J. Med.* 335:624–630 (1996)). These studies suggest that decreasing the number of HCMV infected host cells can benefit certain individuals.

HCMV also has been associated with morbidity and mortality in immunocompromised patients. HCMV is an important consideration in the treatment of patients suffering from Acquired Immunodeficiency Syndrome (AIDS). The defining complication of HCMV is viral retinitis, which, if left untreated, can lead to blindness. Other disease manifestations of HCMV viremia include encephalitis, enteritis and pneumonia. At autopsy there is multi-organ involvement of HCMV disease in the majority of AIDS patients who had severe HCMV retinitis. Historically, HCMV disease has been one of the more devastating of the opportunistic infections that beset HIV-infected individuals whose $CD4^+$ T cell level diminishes below $100/mm^3$.

HCMV can cause opportunistic infections in, for example, immunosuppressed organ transplant patients. Prior to the use of antiviral chemotherapy, HCMV infection had been responsible for a substantial proportion of post-bone marrow transplantation complications (J. Meyers et al., *J. Infect Dis.* 153:478–488 (1986)). The use of drugs such as gancyclovir with substantial anti-HCMV activity have reduced complications associated with post-bone marrow transplant HCMV infections (G. Schmidt et al. *New England J. Med.* 324:1005–1011 (1991); J. M. Goodrich et al., *New England J. Med.* 325:1601–1607 (1991)). However, prophylactic administration of gancyclovir has several negative consequences, including neutropenia and increased numbers of fatal bacterial and fungal diseases. Equally importantly, gancyclovir also delays reconstitution of cellular immunity as well as specific cellular responses to CMV. This results in a complication referred to as "late CMV disease," which arises about 90 days post-transplant. Late CMV disease can result in morbidity or mortality and is most common in patients who have received either prophylactic or therapeutic gancyclovir treatment soon after transplant.

A $CD8^+$ CTL response is believed to be important in a mammalian host response to acute viral infections such as HCMV. The observations that HCMV infection is widespread and persistent, and may be reactivated and become clinically evident in the immunosuppressed patient, suggest that virus-specific T-cells play an important role in the control of persistent infection and the recovery from HCMV disease.

In humans, protection from the development of HCMV disease in immunosuppressed bone marrow transplant recipients correlates with the recovery of measurable $CD8^+$ HCMV-specific class I MHC-restricted T cell responses (Quinnan et al., *N. Eng. J. Med.* 307:7–13 (1982); Reusser et al., *Blood* 78:1373–1380 (1991)). The transfer of donor-derived HCMV-specific $CD8^+$ CTL clones to allergenic bone marrow transplant recipients results in detectable CTL-based HCMV immunity, and statistically significant diminution of HCMV disease after bone marrow transplant (Walter et al., *N. Eng. J. Med.* 333:1038–1044 (1995)). Although successful in application, this approach has the disadvantage that it requires a sophisticated laboratory setup, which is also highly labor-intensive and costly, to derive the HCMV-specific CTL in vitro.

Because human cytomegalovirus is relatively common, yet is associated with some extremely serious health conditions, a vaccine which can reduce disease incidence and severity in a bone marrow transplant recipient, a solid organ transplant, a heart patient, an AIDS patient or a woman of child-bearing years would be highly desirable. Several HCMV vaccines are in development, including live attenuated CMV, CMV proteins carried in attenuated poxviruses and soluble analogs of CMV membrane proteins. Unfortunately, the FDA has not approved any of these vaccines as safe and effective, despite the great efforts made in their development.

Vaccine development using CTL epitopes has become a widely adapted strategy to immunize individuals against infectious diseases and cancer. The specificity of CTL epitopes, and the fact that intracellular protein processing is not required, makes them an attractive alternative to the use of whole proteins as immunogens. To develop such a vaccine, the viral proteins which cause the host to recognize HCMV must be identified.

A variety of antigens, including tumor antigens, viral antigens and self-proteins are processed into peptides which are delivered to MHC Class I for presentation on the surface of antigen presenting cells (Reddehase et al., Nature 337:651–653 (1989); Rosenberg et al., Nat. Med. 4:321–327 (1998); Visseren et al., J. Immunol. 154:3991–3998 (1995)). Since the discovery that 8–12 amino acid fragments of cellular or viral proteins are embedded in the peptide binding groove of MHC Class I, there has been considerable interest in identifying the amino acid sequence of these fragments (Joyce and Nathenson 1994; Rammensee et al. 1993). Some of these peptides have been identified, formulated into vaccines, and evaluated for efficacy against certain viral diseases and cancer (Vitiello et al. 1995; Wang et al. 1990).

The viral life cycle provides insight as to the most effective time frame for targeting a vaccine to maximally disrupt virus production and spread. Following HCMV entry into the host cell and uncoating, the viral genome is expressed sequentially via immediate early (0–2 hour), early (2–24 hour) and late (>24 hour) viral proteins. However, certain viral structural proteins such as pp65 and pp150 are chaperoned into the cell because of their existence in large quantity in the viral particle.

The viral structural protein, pp150, has been identified as a target antigen for HCMV-specific class I MHC restricted CTL derived from the peripheral blood of most asymptomatic HCMV seropositive individuals. CTL against pp150 or pp65 (another matrix protein that is recognized frequently) are able to recognize and lyse HCMV-infected cells in vitro within an hour of infection and in the absence of viral gene expression (Riddell and Greenberg, Curr. Top. Microbiol. Immunol. 189:9–34 (1994)). Thus, CTL against HCMV pp150 are important effector cells to limit HCMV reactivation and progression to disease. The ability to induce such a cellular immune response in both immunocompromised and normal individuals would be extremely important in creating an effective vaccine (Li et al., Blood 83:1971–1979 (1994)). Peptides based on pp65 sequences which are useful for vaccines are described in U.S. Pat. No. 6,074,645, the disclosures of which are hereby incorporated by reference.

Individual MHC Class I molecules preferentially bind peptides of a given motif. The amino acid sequence of specific positions of the motif are invariant, allowing a given peptide to bind to MHC Class I molecules with high affinity. These invariant amino acids are referred to as "anchor positions" (Falk et al., Nature 351:290–296 (1991)). Later studies have suggested that amino acid positions other than the anchor positions also contribute to the specificity of peptide binding to MHC Class I molecules. Additionally, residues at positions within the CTL epitope which do not interact with MHC Class I molecules may interact with T cells, presumably by binding the T Cell receptor (TCR). The binding of amino acid residues to MHC or TCR structures is independently governed, so that substitution of TCR binding amino acid residues in many cases will not interfere with binding to the MHC molecule on the surface of an antigen presenting cell.

Edman degradation followed by N-terminal sequence analysis has been used to sequence the peptides which are bound to the MHC class I peptide binding groove. Mass spectrometry of HPLC-separated peptide mixtures can elucidate the primary sequence of individual peptides. In most cases, the length of these peptides is between 9 and 11 amino acids. Peptide fragments which bind to MHC are referred to as "naturally processed epitopes."

Some workers have attempted to predict which peptides of a given length, between 9–11 amino acids, will optimally bind to individual HLA Class I alleles based solely on their conformity to a motif specific for that allele. (Falk et al., Nature 351:290–296 (1991)). However, these methods do not reliably predict either correct binding or recognition by T cells as a result of endogenous processing of viral protein.

Experience with another HCMV protein, pp65, has indicated that the available motif programs are not sufficiently adept at correctly predicting sequences which are recognized by human T-cells specific for an immunogenic viral protein. Identification of naturally processed epitopes generally requires brute-force approaches, including truncation analysis, overlapping peptides, and peptide deletions consisting of single amino acid removal from either the amino or carboxyl terminus followed by assay for recognition and binding. Therefore, epitope mapping is almost completely empirical. Andersen et al., Tissue Antigens 55:519–531 (2000).

CTL are an important means by which a mammalian organism defends itself against infection by viruses and possibly cancer. A processed form of antigen, such as a viral protein minimal cytotoxic epitope, is recognized by T cells in combination with MHC Class I molecules. Functional studies of viral and tumor-specific T cells have confirmed that a minimal cytotoxic epitope consisting of a peptide of 8–12 amino acids can prime an antigen presenting cell to be lysed by $CD8^+$ CTL, as long as the antigen presenting cell presents the epitope in the context of the correct MHC molecule.

The route of entry of a protein into the cell determines whether it will be processed as an antigen bound to either MHC Class I or Class II molecules. The endogenous or Class I pathway of protein degradation is often used by cells when infectious viruses are present. Viral nucleoproteins are processed within the cell, and degraded portions are transported to the surface via MHC Class I molecules. Viral envelope glycoproteins, because they are cell surface molecules, do not obligatorily induce CTL recognition. Viral nucleoproteins, predominantly in the form of processed epitopes, frequently are the target antigens recognized by $CD8^+$ CTL (Townsend et al., Philos. Trans. R. Soc. Lond. (Biol). 323:527–533 (1989)).

Antigens entering the cell through exogenous pathways (pinocytosis, etc.) typically are not processed and presented by Class I MHC molecules. Methods to introduce proteins directly into the cytoplasm, therefore, have become one focus of vaccine developers. Recombinant vaccinia viruses can be used to infect cells, delivering a large amount of intracellular antigen, however these viruses themselves have the potential to cause disease in immunosuppressed people, such as bone marrow transplant recipients or AIDS patients. Attenuated vaccinia viruses, such as modified vaccinia ankara or canary pox viruses offer an alternative to immunosuppressed individuals with respect to delivery of antigens and proteins. Recent published reports have advocated the use of epitope vaccines in the minimal form, whether they are delivered as proteins made from viruses, or utilizing minimal epitope in the form of peptides. Ishioka et al., J.

Immunol. 162:3915–3925 (1999); Fu, J. Virol. 72(2):1469–1481 (1998); Rodriguez et al., J. Virol. 72(6):5174–5181 (1998). Another approach to vaccination is to mix an antigenic protein with an adjuvant and introduce the mixture under the skin by subcutaneous injection.

Another potential approach to elicit cytotoxic T lymphocytes is to use the minimal cytotoxic epitope defined for a specific viral antigen in the context of a particular MHC restriction element to boost a T cell memory response to the virus. The ability of a minimal cytotoxic epitope to provide protective immunity to challenge by a lethal dose of an infectious virus has been discussed in the literature. Vaccine developers have developed increasing interest in utilizing the minimal cytotoxic epitope as the vaccine because it is capable of binding to MHC Class I molecules through external binding of the cell surface molecules without the need for internalization or processing.

Minimal cytotoxic epitopes generally have been most effective when administered in the form of a lipidated peptide together with a helper CD4 epitope (Vitiello et al., J. Clin. Invest. 95:341–349 (1995) and Livingston et al., J. Immunol. 159:1383–1392, 1997)). Peptides administered alone, however, also can be highly effective. Other vaccine modifications which have been discussed include inclusion of a signal sequence such as KDEL for endoplasmic reticulum retention and targeting to attain maximum activity. There is also evidence in the literature that a minimal cytotoxic epitope presented by particular types of antigen presenting cells (e.g. dendritic cells) may cause a primary immune response to occur in the absence of viral infection or prior contact with the virus or tumor cell.

The peptides and functional sequence variants thereof can be formulated as a vaccine as a chimeric lipidated peptide or a chimeric peptide with a covalently bound HTL epitope at the amino terminus. The HTL epitope can be any peptide that has broad reactivity to human MHC class II to stimulate a classic helper response. Such molecules include but are not limited to amino acids 830–843 from tetanus toxin (P. Panina-Bordignon et al., Eur. J. Immun. 19:2237–2242 (1989)), HTL epitopes from HIV envelope protein (J. A. Berzofsky et al., J. Clin. Invest. 88:876–884 (1991)), or a synthetic version (PADRE) predicted from known anchor residues (J. Alexander et al., Immunity 1:751–761 (1994)).

The lipidation of the HTL+CTL epitope preferably is performed on the amino terminus of the HTL epitope, with the HTL epitope being amino terminal to the CTL epitope. Suitable lipid moieties are known and described in the literature. (H. Schild et al., Eur. J. Immunol. 21:2649–2654 (1991); A. Vitiello et al., J. Clin. Invest. 95:341–349 (1995); K. Deres et al., Nature 342:561–564 (1989)). Alternatively, the CTL epitope can be lipidated at its amino terminus, followed by the HTL epitope, or the lipid can be attached at the carboxyl terminus followed by either the CTL or HTL epitope(s). Unlipidated vaccines, as well as mono-, di- and tri-lipidated vaccines are contemplated for use with the present invention. A three amino acid spacer can be inserted between the HTL and CTL epitope, or the epitopes can be fused directly in frame. Alternatively the CTL epitope lipidated on its amino terminus can be administered together with the HTL epitope, without covalent attachment.

In spite of significant efforts to identify the particular HCMV antigens and epitopes that are recognized by CTL, these naturally processed epitopes, along with effective methods of preventing and treating HCMV infection are not commercially available. Therefore, a peptide-based vaccine for this clinically important disease would be of enormous value.

SUMMARY OF THE INVENTION

Accordingly, the present invention comprises peptides according to SEQ ID NOS: 1 and 2. In a further embodiment, the invention comprises vaccines against human cytomegalovirus comprising a peptide selected from the group consisting of SEQ ID NOS: 1 and 2.

In yet a further embodiment, this invention comprises a cellular vaccine against human cytomegalovirus which comprises antigen presenting cells that present a peptide selected from the group consisting of SEQ ID NO: 1 and 2.

In yet a further embodiment, the invention comprises a recombinant viral vector which expresses a gene encoding a peptide according to SEQ ID NO: 1 or 2.

In yet a further embodiment, the invention comprises methods of modulating the immune response to human cytomegalovirus infection which comprises administering a vaccine or a cellular vaccine as described above.

In yet a further embodiment, the invention provides a method of vaccinating a mammal in need thereof against human cytomegalovirus which comprises administering to said mammal a vaccine or a cellular vaccine as described above.

In yet further embodiments, the invention provides vaccines against human cytomegalovirus which comprise a peptide selected from the group consisting of SEQ ID NO: 1 and SEQ ID NO: 2 and an adjuvant, preferably a DNA adjuvant.

In yet a further embodiment, the invention provides an immunological reagent which comprises a peptide selected from the group consisting of SEQ ID NO:1 and SEQ ID NO: 2.

DETAILED DESCRIPTION OF THE PREFERRED EMBODIMENTS

The present invention is directed toward peptides which are useful for creating effective vaccines against HCMV. These peptide vaccines are able to elicit a cellular immune response against HCMV-infected cells because they are the exact epitopes which are recognized by the immune cells of persons who have been infected with HCMV and have mounted a successful response to the infection. These peptides therefore are able to stimulate effective killing of HCMV infected cells and have done so in infected, asymptomatic persons. The peptides of this invention are the epitopes which are routinely and successfully presented on the surface of antigen presenting cells in the human host, guaranteeing productive binding to MHC Class I and the elicitation of a cellular immune response to HCMV in human beings.

Truncations of the pp150 protein expressed in vaccinia viruses were screened against pp150-specific T cell clones. These CTL clones were established from HCMV-seropositive volunteers using established methods. (Walter et al., N. Eng. J. Med. 333(16):1038–1044 (1995); McLaughlin-Taylor et al., J. Med. Virol. 43:103–110 (1994); Yee et al., J. Immunol. 157(9):4074–4086 (1996); Diamond et al., Blood, 90:1751–1767 (1997); LaRosa et al., Blood 97:1776–1786 (2001)). Recombinant vaccinia viruses having successive amino and carboxyl terminal deletions of approximately 100–200 nucleotides over the entire pp150 gene were tested for the ability to sensitize cells for killing by the pp150-specific T cells. Progressively smaller truncated peptides covering the length of the identified sequence were tested until a narrow area of the protein was identified as containing the peptide which mediated the cytotoxic T cell response of that clone. When a peptide no longer than 100 amino acids was identified, a series of overlapping peptides covering the length of the identified sequence were synthesized for further analysis. Using these methods, a scan of the 100 amino acid sequence using 15mer peptides overlapping by three amino acids required a total of 20 peptides.

For the test, autologous and HLA mismatched (control) lymphocyte cell lines were sensitized with the scanning peptides at a concentration of 50 µM for 1–2 hours, and washed. The relevant CTL then were incubated with chromated EBVLCL (Epstein-Barr virus transformed lymphocyte cell lines) sensitized with peptide, and a standard chromium release assay was performed. The sensitivity of lysis was determined, and any positive peptide was further truncated, both at the amino and carboxyl termini, until a minimal cytotoxic epitope that corresponds to the HLA allele of that T cell clone was defined. Table I provides peptide epitopes which are naturally processed from pp150 by persons having the indicated HLA allele.

TABLE 1

HLA Restriction and Sequence of CTL Epitopes from HCMV pp150.

| HLA Allele Restriction Element | SEQ Sequence of ID HLA Epitope NO. | Location of CTL Epitope | Number of Individuals Tested |
|---|---|---|---|
| HLA A*0301 | TTVYPPSSTAK 1 | 945–955 | 2/2 |
| HLA A*6801/2 | QTVTSTPVQGR 2 | 792–802 | 2/2 |

The vaccine epitopes, regardless of primary structure, may be injected s.c. into the forearm or other body location in a standard formulation buffer (PBS/10% DMSO or higher concentration/0.01% triflouroacetic acid or other acid or alcohol of the same or different concentration) once. Vaccines may be administered in PBS or any other pharmaceutically compatible vehicle. Three to six weeks later, a booster injection of the same material may be administered. Multiple booster injections spaced three to six weeks apart can be subsequently administered, if necessary.

Vaccines can be administered to a patient or at-risk individual, or to the donor of a bone marrow transplant, who is either positive or negative for the virus. Illustrative examples of vaccine peptides include:

| N-terminal | C-terminal |
|---|---|
| (Pam)$_2$-KSS*QYIKANSKFIGITE*<u>AAA</u>TTVYPPSSTAK | (SEQ ID NO: 3) |
| (Pam)$_2$-KSS*AKXVAAWTLKAAA*TTVYPPSSTAK | (SEQ ID NO: 4) |
| (Pam)$_1$-KSS*QYIKANSKFIGITE*<u>AAA</u>QTVTSTPVQGR | (SEQ ID NO: 5) |
| (Pam)$_1$-KSSQTVTSTPVQGR<u>GGG</u>*QYIKANSKFIGITE* | (SEQ ID NO: 6) |
| TTVYPPSSTAK<u>AAA</u>*AKXVAAWTLKAAA* | (SEQ ID NO: 7) |
| KDELQTVTSTPVQGR*QYIKANSKFIGITE* | (SEQ ID NO: 8) |
| *QYIKANSKFIGITE*TTVYPPSSTAKKDEL | (SEQ ID NO: 9) |
| *AKXVAAWTLKAAA*QTVTSTPVQGR | (SEQ ID NO: 10) |
| *VSTIVPYIGPALNI*<u>AAA</u>TTVYPPSSTAK | (SEQ ID NO: 11) |
| TTVYPPSSTAK<u>AAA</u>*VSTIVPYIGPALNI* | (SEQ ID NO: 12) |
| *VSTIVPYIGPALNI*<u>AAA</u>QTVTSTPVQGR | (SEQ ID NO: 13) |
| QTVTSPVQGR<u>AAA</u>*VSTIVPYIGPALNI* | (SEQ ID NO: 14) |
| TTVYPPSSTAK | (SEQ ID NO: 1) |
| QTVTSTPVQGR | (SEQ ID NO: 2) | wherein X is cyclohexylalanine or phenylalanine and "Pam" is palmitic acid. The three-A or alternative structural spacer (underlined) may be interchanged among vaccine peptides. The format of the peptides shown above can be described (from the amino terminus) as: lipid-KSS—HTL epitope (italics)—amino acid spacer (underlined)—CTL epitope. The positions of the CTL and HTL epitopes may be interchanged. The CTL epitope (or a functional sequence variant thereof) may be further modified by adding a leader sequence and/or the amino acids KDEL may be appended to the carboxyl terminus to assist retention and targeting into the endoplasmic reticulum as exemplified in SEQ ID NO: 8. Palmitic acid or any suitable lipid may be used, including but not limited to stearic acid, myristic acid, lauric acid, capric acid and decanoic acid. Preferred lipid moieties include palmitic acid. Alternatively, forms of the vaccine without lipids may be used, choosing the appropriate T-helper epitope that causes immunogenicity either with or without accompanying adjuvants. Sequences such as KSS may be included at the amino terminus of unlipidated peptides to aid in solubility. Other vaccine formulations include peptides having the dextro form of the amino acid on the N-terminus. Unlipidated vaccines do not require the KSS linker sequence.

Adjuvants may form part of the vaccine formulation. Adjuvants such as complete or incomplete Freund's adjuvant, aluminum hydroxide or the like are contemplated, however a preferred adjuvant, particularly for use in humans, is a DNA adjuvant. Single-stranded DNA adjuvants comprising specific sequences including Cytosine-phosphate-Guanosine (CpG) are known in the art and are contemplated for use with this invention. DNA adjuvants lacking these CpG sequences also are useful with the invention. An exemplary DNA adjuvant may comprise a 20mer of nucleotides with 2 CpG motifs, or any DNA oligomer, generally about 20 to about 25 nucleotides long. Increased stability of the sequence may be obtained by substituting phosphate groups in the nucleotide backbone with thioate groups to create a phosphoro-thioate backbone rather than a phosphoro-diester backbone.

Vaccines of this invention also may be formulated as DNA vaccine. Suitable vaccines include recombinant viral vectors, for example pox virus, which express a gene encoding one or more HCMV peptides or analogs of the invention. These vaccines may be constructed according to methods known in the prior art. In summary, these peptides may be administered as a vaccine, alone or combined with other peptide sequences, in the presence or absence of an adjuvant. Alternatively, a minimal CTL epitope from an immunogenic protein that is delivered utilizing a virus or DNA construct may also induce CTL responses which have been shown to be important for virus reduction and elimination.

The peptides of this invention also may be used in immunological methods to detect pp150-reactive CTL in a patient or a sample from a patient. Assays such as chromium release assays as described below or any known assay is suitable. Specific T cell clones which recognize pp150 peptide may be detected using an immunological reagent comprising the peptides according to SEQ ID NO: 1 or 2, for example, tetramer reagents such as those described in Altman et al., Science 274:94–96, 1996 or U.S. Pat. No. 5,734,023, the disclosures of which are hereby incorporated by reference, or dimer reagents such as those described in La Rosa et al., Blood 97(6):1776–1786, 2001 and Greten et al., Proc. Natl. Acad. Sci. USA 95:7568–7573, 1998, the disclosures of which are hereby incorporated by reference.

MHC tetramers generally are known in the art and consist of tetrameric complexes of beta-2 microglobulin, a biotinylated MHC class I molecule conjugated to streptavidin linked to a fluorescent marker, and an antigenic peptide such as, for example, a pp150 peptide or the like. The MHC class I allele and the peptide in combination allow specific recognition of T cells which recognize that peptide antigen in the context of the class I allele. Multiple complexes are often linked together to increase binding, since the affinity of the individual complex is generally low. Using a fluorescently labeled tetramer, specifically binding T cells may be separated using known techniques, such as fluorescent activated cell sorting and the like. Dimeric complexes of the same diagnostic reagents taking advantage of pp150 peptide antigens also may be used.

Those of skill in the art are familiar with the use of such dimer and tetramer reagents and are fully able to construct and use such reagents for use in various diagnostic methods known in the art. As well, those of skill in the art can readily synthesize useful reagents or variants of these reagents.

The following examples are intended to illustrate rather than limit the appended claims.

EXAMPLES

Example 1

Derivation of HCMV-Specific T-cell Clones

Forty to fifty milliliter samples of whole peripheral blood were obtained from HCMV seropositive volunteers (detected by standard antibody methods). Whole blood was sedimented for 10 minutes at 1400 rpm in a tabletop centrifuge and red blood cells removed. The white blood cells (WBCs) were separated using Ficoll-HyPaque (DuPont) density gradient centrifugation as follows. The buffy coat was diluted to 12 ml with phosphate buffered saline, and 6 ml were layered on top of Ficoll-HyPaque. After centrifugation at 2000 rpm in a tabletop centrifuge for 15–30 minutes, the interface containing the white blood cells was removed, diluted in PBS and pelleted for 8–12 minutes at 1000 rpm. The cells were again resuspended in PBS and washed as above one additional time. The white blood cells were resuspended at 4–5 million cells/ml in T cell medium (TCM) containing human serum obtained from pooled AB+ (blood group) HCMV seronegative donors.

Example 2

Derivation of LCL Antigen-Presenting Cells

Simultaneously, an autologous antigen presenting cell line was prepared by Epstein Barr virus immortalization of peripheral blood leukocytes according to methods in Current Protocols in Immunology, Unit 7.22, Wiley-Liss Press (1993). The cytotoxic T lymphocytes and antigen presenting cells were derived from the same individual to ensure HLA matching between the cell lines.

Example 3

In vitro Stimulation of T Cell Clones by HCMV

To initiate the in vitro stimulation of the T cells, a monolayer of autologous dermal fibroblasts obtained from the same volunteers as the white blood cells was established by plating the cells in 12-well plates at $10^5$ cells/ml/well in DMEM containing 10% human AB+ serum for 24 hours. After 24 hours in culture, the fibroblasts were infected with HCMV virions (AD169 or Towne strain) for 2 hours at a multiplicity of infection of between 1 and 5. The medium and virus were aspirated from the monolayer, and 1 ml of fresh medium was added. The monolayer was incubated in the medium for an additional 4 hours, following which time the medium was aspirated. Two milliliters of medium containing 8–10 million white blood cells were added to each well containing HCMV infected fibroblasts. The white blood cells and fibroblasts were cultured in RPMI-1640 (Irvine Scientific) containing 50 U/ml penicillin, 50 $\mu$g/ml streptomycin, 4 mM L-glutamine, 25 $\mu$M 2-mercaptoethanol, 10 mM HEPES and 10% human AB+ serum. The cells were co-incubated for 7 days. Serum was replaced if it became spent, or the culture expanded if there was vigorous cell growth.

The white blood cells were re-stimulated on day 7 by plating onto a fresh monolayer of HCMV-infected autologous fibroblasts prepared as described above. In addition, γ-irradiated (2500 rad) autologous peripheral blood leukocytes (5-fold over WBC) were added as feeder cells, and the medium was supplemented with recombinant IL-2 (10 IU/ml, Chiron-Cetus) on days 2 and 4 of this second stimulation. Wells that exhibited rapid cell growth were supplied with new medium containing IL-2 as the medium became spent. After 12–16 days in culture, the cells were harvested and assayed for recognition of HCMV matrix proteins in a chromium release assay.

Example 4

Chromium Release Assay

Autologous or HLA-mismatched (control) target antigen presenting cells by infection with recombinant vaccinia viruses containing the DNA for HCMV pp150 or wild-type virus, strain WR, were prepared. After overnight infection, the antigen presenting cells were incubated with chromium-51, and the assay was carried out according to known methods. In the chromium release assay, the vaccinia-infected target cells were loaded with chromium-51 and then mixed with T-cells (effector cells). Preferably, the cells were mixed at a series of effector:target (E:T) cell ratios varying from 20:1 to 1:1. After a 4 hour incubation period, the medium in which the cells were incubated was harvested. The release of radioactivity into the medium ($R_e$) was quantitated with a gamma scintillation counter. The extent to which infected antigen presenting cells exhibit spontaneous lysis and the release of radioactivity ($R_s$) in the absence of cytotoxic T lymphocytes was established for each virus vector. The maximum amount of radioactivity incorporated into and releasable by the target cells ($R_{max}$) was established by lysis of target cells in a detergent (1% Triton X100; Sigma) solution. Percentage cytotoxicity was expressed as:

$$100 \times ((R_e)-(R_s))/((R_{max})-(R_s)).$$

Assays were deemed unacceptable and were repeated unless spontaneous release ($R_s$) was less than 30%. A positive result for pp150 indicates that, in the tested polyclonal population, there are T cells which recognize the pp150 HCMV protein expressed by the virus.

Example 5

Derivation of CTL Clones Utilizing pp150 Infected Fibroblasts

An additional method to derive CTL is to create autologous antigen presenting cells, expressing a recombinant form of HCMV proteins, including pp150. A mono-layer of fibroblasts as described in Example 1 is infected with pp150 Vac and the virus is allowed to propagate on the cells for several hours. The monolayer is washed and irradiated using a Stratalinker™ apparatus (Stratagene, LaJolla, Calif.). This procedure inactivates further growth of the vaccinia virus however, allowing expression to continue. White blood cells are added to the monolayer as described in Example 3. This stimulation is directed at one HCMV protein and focuses the immune response specifically to pp150.

Example 6

Identification of the CTL Epitope

White blood cells stimulated two times by HCMV on dermal fibroblasts or by pp150Vac-infected fibroblasts were cloned by limiting dilution in 96 well U-bottom plates. The white blood cells were depleted of CD4+ T cells using paramagnetic beads conjugated to anti-CD4 antibodies. The resulting population was generally between 90–95% CD8+, a reliable T cell subset marker, and generally 99% CD3+, a marker for most peripheral blood T cells, as assayed by either flow cytometry or fluorescence microscopy. This final population was plated at a concentration between 0.3–3 cells per well in a final volume of 150 µl. Each well also contained γ-irradiated 1.0–3.0×10$^5$ allogeneic peripheral blood mononuclear cells in T cell medium containing human AB+ serum supplemented with 50–100 IU/ml recombinant IL-2 (Chiron-Cetus) and 0.5 µg/ml PHA (Murex).

After 3 days of culture, the PHA was diluted 2-fold by exchanging 75 µl with fresh culture medium supplemented with rIL-2. The wells were supplemented with fresh rIL-2 every 3–4 days, and medium was replaced as necessary. The cells were restimulated at between 12–14 days with fresh allogeneic peripheral blood mononuclear cells as described above, and the plates were carefully observed for growth in individual wells. Visible cell growth indicated the need to transfer the expanding T cells to larger wells. T cells were restimulated every two weeks, and were transferred to progressively larger wells.

At the stage of accumulation of several million cells, some were cryopreserved, and others were used for chromium release assays. The target cells were HCMV infected fibroblasts, uninfected fibroblasts, or autologous lymphocyte cells lines infected with either wild type vaccinia or vaccinia virus expressing pp150 or truncated pp150. HLA mismatched fibroblasts and lymphocytes were used as controls. T cell clones which were both HCMV and pp150-specific, and reactive only to autologous targets were selected as positive. T cell clones with different HLA phenotypes were isolated in the same way, using initial peripheral blood samples from volunteers having different HLA genotypes. By repeating this method using target cells presenting smaller and smaller portions of pp150, including synthetic 15–20 amino acid peptides taken from pp150 and deletions thereof, the minimal cytotoxic epitope for that particular HLA allele was discovered.

The purity of all peptides was confirmed by HPLC on a Vydac $C_{18}$ column using acetonitrile/TFA as the moving phase. Preferably, peptides should be 70–80% pure or more and the CD8+ status, characteristic of CTL which recognize Class I restricted peptides, should be confirmed.

Example 7

Immunization of Bone Marrow Transplant Patients

A therapeutically active form of an antigenic peptide according to the present invention is administered to an HCMV-seropositive bone marrow transplant donor at a sufficient time before donation of the tissue (six to eight weeks, for example) in single or multiple doses separated by a given number of days or weeks prior to bone marrow transplant to enable the development of an anti-HCMV cellular immune response. The antigenic peptide can be made in accordance with the parameters described in the specification or according to any known method, and administered with or without an adjuvant. Preferably, multiple doses are given. If an unmanipulated bone marrow graft is to be given to the recipient, such a graft will contain 25% or more of mature T cells. The T cells present in the immunized donor's bone marrow will confer active immunity to the bone marrow transplant recipient. Alternatively, when a T cell-depleted bone marrow graft is to be employed, an aliquot of T cells from the immunized donor can be administered to the patient following (for example, approximately 21 to 35 days) transplantation in order to provide the recipient patient with HCMV immunity.

Example 8

Immunization of Healthy Adult Women of Child-bearing Years

A therapeutic form of antigenic peptide according to the present invention is administered to a HCMV-negative or HCMV-positive women of child-bearing years either before or after conception. A vaccine comprising a single or multi-epitope vaccine prevents or reduces primary HCMV infection of the fetus and of children who may come in contact with the woman. The vaccine is used to prevent new HCMV infection, or to limit existing infection which may be damaging to the developing fetus.

Example 9

Recognition of Modified Vaccinia Ankara (MVA) Infected EBV-LCL

Recombinant modified Vaccinia Ankara (MVA) expressing HCMV pp150 were used to infect EBV LCL from individuals who had the HLA A*0301 allele or the A*68xx allele. T-cell clones specific for the epitopes of SEQ ID NOS: 1 and 2 were able to recognize these targets in a chromium release assay performed as described for Example 3. Very substantial lysis (>60% specific cytotoxicity) was seen, with specificity more than 5 fold greater than that seen with targets expressing wild-type MVA.

Example 10

Screening for CMV Immunity with HLA Tetramer Reagents Complexed to CMV Peptides Peripheral blood is collected from human donors and recipients of allogeneic hematopoietic stem cell transplant (HSCT) after obtaining consent. Study participants conveniently may be related sibling donors and recipients undergoing allogeneic HSCT for hematologic malignancies including myelodysplasia. The donors and/or the recipients are CMV seropositive, and all are HIV-negative. Donor samples are drawn prior to administration of granulocyte colony stimulating factor (GCSF), and 3–5 days later, at the time of cell harvest for transplant. Recipient blood samples are taken 40, 90, 120, 150 and 180 days after transplant (stem cell infusion). Monitoring for CMV reactivation is done twice weekly as part of routine patient management by both PCR and blood culture shell vial assay on plasma samples. When CMV reactivation is detected (defined as two positive PCR assays or one positive blood culture result) the patient is treated with prophylactic gancyclovir for 6 weeks.

Peripheral mononuclear cells (PBMC) are isolated by standard density gradient centrifugation from heparinized blood, washed, resuspended in FCS (Hyclone, Logan, TU) with 10% DMSO, aliquoted and cryopreserved in liquid $N_2$. Studies are performed on PBMC that have been thawed and assayed directly with no cultivation or stimulation in vitro. Cells are labeled with HLA A*0301 (A3) or HLA A*6801 (A68) tetrameric reagents prepared as follows. Tetrameric reagents are refolded and purified using known methods. Conveniently, the reagents may be prepared using a minor modification of the procedure used by the NIAID Tetramer Core Facility (www.emory.edu/WHSC/YERKES/VRC/tetramer.html). Briefly, A3 or A68 heavy chain and beta-2-microglobulin ($\beta_2$M), cloned in the vector pHN1, are expressed in *E. coli* XA90 and refolded with the peptides SEQ ID NO:1 or 2, respectively. The refolded HLA-A3 or A68/$\beta_2$M/peptide complexes are biotinylated using the enzyme BirA (Avidity Inc.) and then purified by FPLC using a Sephacryl S300 gel filtration column, followed by a MonoQ ion exchange column. The purified biotinylated HLA-A3 or A68/$\beta_2$M/peptide complexes are conjugated to either streptavidin-PE (Pharmingen) or to streptavidin-APC (Molecular Probes). Labeling of cells typically is performed using 0.5 µg tetramer to stain 0.5–1.0 million cells in a 50–100 µl volume of PBS/0.5% BSA for 20 minutes. The cells then are washed and analyzed on a FACScalibur™ (BDIS) flow cytometer. A lymphocyte gate is set based on forward and side scatter and a minimum of 30,000 gated events captured. Quadrants are set based on the negative controls and the number of tetramer-positive cells is expressed as a percentage of the lymphocyte population.

Example 11

Detection of IFN-γ Production by Lymphocytes on Peptide Stimulation

Thawed aliquots of PBMC are washed with cold buffer (PBS/0.5% BSA) and labeled with tetrameric reagents prepared as described in Example 10 or by any convenient method for 20 minutes. The cells then are washed, resuspended in 1 ml RPMI-1640 (Irvine Scientific) supplemented with 10% FCS and incubated overnight at 37° C. in a 5% $CO_2$ incubator. Brefeldin A (GolgiPlug™, Pharmingen) is added to 1 µM after 1 hour. To some aliquots, viral epitope peptides (SEQ ID NO:1 or 2) are added at 10 µg/ml and to others, an irrelevant HLA-restricted peptide is added as a negative control. The following day, the cells are washed and sub-aliquoted into individual 12×75 mm tubes at 1×10⁶ cells per aliquot. The cells are labeled with FITC-conjugated antibody to CD8 (Pharmingen) by incubation for 20 minutes at 4° C. in 50 µl buffer. The cells then are washed, fixed and permeabilized (Cytofix/Cytoperm, Pharmingen, La Jolla, Calif.) before labeling with 5 µl APC-conjugated antibody to IFN-γ for 20 minutes at 4° C. The labeled cells are washed and analyzed by flow cytometry.

---

What is claimed is:

1. A peptide according to SEQ ID NO: 1.
2. A peptide according to SEQ ID NO: 2.
3. A vaccine against human cytomegalovirus which comprises a peptide selected from the group consisting of SEQ ID NO: 1 and SEQ ID NO: 2.
4. A vaccine according to claim 3, which further comprises an adjuvant.
5. A vaccine according to claim 4, wherein said adjuvant is a DNA adjuvant.
6. A vaccine against human cytomegalovirus which comprises a peptide selected from the group consisting of SEQ ID NO: 1 and SEQ ID NO: 2 and a DNA adjuvant.
7. A cellular vaccine against human cytomegalovirus which comprises antigen presenting cells which present a peptide selected from the group consisting of SEQ ID NO: 1 and SEQ ID NO: 2.
8. A method of modulating the immune response to human cytomegalovirus infection, which comprises administering a vaccine according to claim 3.
9. A method of modulating the immune response to human cytomegalovirus infection, which comprises administering a vaccine according to claim 7.
10. A method of vaccinating a mammal in need thereof against human cytomegalovirus, which comprises administering to said mammal a vaccine according to claim 3.
11. A method of vaccinating a mammal in need thereof against human cytomegalovirus, which comprises administering to said mammal a vaccine according to claim 7.
12. A recombinant viral vector which contains a gene encoding a peptide selected from the group consisting of SEQ ID NO: 1 and SEQ ID NO: 2.
13. A diagnostic reagent which comprises a peptide selected from the group consisting of SEQ ID NO: 1 and SEQ ID NO: 2 and which further comprises a label.
14. A diagnostic reagent according to claim 13, which comprises a complex of beta-2 microglobulin, a biotinylated MHC class I molecule conjugated to streptavidin linked to a fluorescent marker, and a peptide selected from the group consisting of SEQ ID NO: 1 and SEQ ID NO: 2.
15. A diagnostic reagent according to claim 14, wherein said complex is a tetrameric complex.
16. A diagnostic reagent according to claim 14, wherein said complex is a dimeric complex.

* * * * *

SEQUENCE LISTING

<160> NUMBER OF SEQ ID NOS: 14

<210> SEQ ID NO 1
<211> LENGTH: 11
<212> TYPE: PRT
<213> ORGANISM: Human cytomegalovirus

<400> SEQUENCE: 1

Thr Thr Val Tyr Pro Pro Ser Ser Thr Ala Lys
1               5                   10

<210> SEQ ID NO 2
<211> LENGTH: 11

```
<212> TYPE: PRT
<213> ORGANISM: Human cytomegalovirus

<400> SEQUENCE: 2

Gln Thr Val Thr Ser Thr Pro Val Gln Gly Arg
1               5                   10

<210> SEQ ID NO 3
<211> LENGTH: 31
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide
<221> NAME/KEY: LIPID
<222> LOCATION: (1)..(1)
<223> OTHER INFORMATION: di-palmitic acid

<400> SEQUENCE: 3

Lys Ser Ser Gln Tyr Ile Lys Ala Asn Ser Lys Phe Ile Gly Ile Thr
1               5                   10                  15

Glu Ala Ala Ala Thr Thr Val Tyr Pro Pro Ser Ser Thr Ala Lys
            20                  25                  30

<210> SEQ ID NO 4
<211> LENGTH: 27
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide
<221> NAME/KEY: VARIANT
<222> LOCATION: (6)..(6)
<223> OTHER INFORMATION: X = cyclohexylalanine or phenylalanine
<221> NAME/KEY: LIPID
<222> LOCATION: (1)..(1)
<223> OTHER INFORMATION: di-palmitic acid

<400> SEQUENCE: 4

Lys Ser Ser Ala Lys Xaa Val Ala Ala Trp Thr Leu Lys Ala Ala Ala
1               5                   10                  15

Thr Thr Val Tyr Pro Pro Ser Ser Thr Ala Lys
            20                  25

<210> SEQ ID NO 5
<211> LENGTH: 31
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide
<221> NAME/KEY: LIPID
<222> LOCATION: (1)..(1)
<223> OTHER INFORMATION: palmitic acid

<400> SEQUENCE: 5

Lys Ser Ser Gln Tyr Ile Lys Ala Asn Ser Lys Phe Ile Gly Ile Thr
1               5                   10                  15

Glu Ala Ala Ala Gln Thr Val Thr Ser Thr Pro Val Gln Gly Arg
            20                  25                  30

<210> SEQ ID NO 6
<211> LENGTH: 31
<212> TYPE: PRT
<213> ORGANISM: Artificial Sequence
```

```
<220> FEATURE:
<221> NAME/KEY: misc_feature
<222> LOCATION: ()..()
<223> OTHER INFORMATION: Human cytomegalovirus vaccine peptide
<221> NAME/KEY: LIPID
<222> LOCATION: (1)..(1)
<223> OTHER INFORMATION: palmitic acid

<400> SEQUENCE: 6

Lys Ser Ser Gln Thr Val Thr Ser Thr Pro Val Gln Gly Arg Gly
 1               5                  10                  15

Gly Gln Tyr Ile Lys Ala Asn Ser Lys Phe Ile Gly Ile Thr Glu
                20                  25                  30

<210> SEQ ID NO 7
<211> LENGTH: 27
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide
<221> NAME/KEY: VARIANT
<222> LOCATION: (17)..(17)
<223> OTHER INFORMATION: X = cyclohexylalanine or phenylalanine

<400> SEQUENCE: 7

Thr Thr Val Tyr Pro Pro Ser Ser Thr Ala Lys Ala Ala Ala Lys
 1               5                  10                  15

Xaa Val Ala Ala Trp Thr Leu Lys Ala Ala Ala
                20                  25

<210> SEQ ID NO 8
<211> LENGTH: 29
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide

<400> SEQUENCE: 8

Lys Asp Glu Leu Gln Thr Val Thr Ser Thr Pro Val Gln Gly Arg Gln
 1               5                  10                  15

Tyr Ile Lys Ala Asn Ser Lys Phe Ile Gly Ile Thr Glu
                20                  25

<210> SEQ ID NO 9
<211> LENGTH: 29
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide

<400> SEQUENCE: 9

Gln Tyr Ile Lys Ala Asn Ser Lys Phe Ile Gly Ile Thr Glu Thr Thr
 1               5                  10                  15

Val Tyr Pro Pro Ser Ser Thr Ala Lys Lys Asp Glu Leu
                20                  25

<210> SEQ ID NO 10
<211> LENGTH: 24
<212> TYPE: PRT
<213> ORGANISM: Artificial Sequence
<220> FEATURE:
```

```
<221> NAME/KEY: misc_feature
<222> LOCATION: ()..()
<223> OTHER INFORMATION: Human cytomegalovirus vaccine peptice
<221> NAME/KEY: VARIANT
<222> LOCATION: (3)..(3)
<223> OTHER INFORMATION: X = cyclohexylalanine or phenylalanine

<400> SEQUENCE: 10

Ala Lys Xaa Val Ala Ala Trp Thr Leu Lys Ala Ala Ala Gln Thr Val
1               5                   10                  15

Thr Ser Thr Pro Val Gln Gly Arg
            20

<210> SEQ ID NO 11
<211> LENGTH: 28
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide

<400> SEQUENCE: 11

Val Ser Thr Ile Val Pro Tyr Ile Gly Pro Ala Leu Asn Ile Ala Ala
1               5                   10                  15

Ala Thr Val Tyr Pro Pro Ser Ser Thr Ala Lys
            20                  25

<210> SEQ ID NO 12
<211> LENGTH: 28
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide

<400> SEQUENCE: 12

Thr Thr Val Tyr Pro Pro Ser Ser Thr Ala Lys Ala Ala Ala Val Ser
1               5                   10                  15

Thr Ile Val Pro Tyr Ile Gly Pro Ala Leu Asn Ile
            20                  25

<210> SEQ ID NO 13
<211> LENGTH: 28
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide

<400> SEQUENCE: 13

Val Ser Thr Ile Val Pro Tyr Ile Gly Pro Ala Leu Asn Ile Ala Ala
1               5                   10                  15

Ala Gln Thr Val Thr Ser Thr Pro Val Gln Gly Arg
            20                  25

<210> SEQ ID NO 14
<211> LENGTH: 27
<212> TYPE: PRT
<213> ORGANISM: Artificial Sequence
<220> FEATURE:
<221> NAME/KEY: misc_feature
<222> LOCATION: ()..()
<223> OTHER INFORMATION: Human cytomegalovirus vaccine peptide
```

-continued

```
<400> SEQUENCE: 14

Gln Thr Val Thr Ser Pro Val Gln Gly Arg Ala Ala Ala Val Ser Thr
1               5                   10                  15

Ile Val Pro Tyr Ile Gly Pro Ala Leu Asn Ile
                20                  25
```